United States Patent
Sullivan et al.

(10) Patent No.: US 12,357,224 B1
(45) Date of Patent: Jul. 15, 2025

(54) METHODS AND APPARATUS FOR NON-INVASIVE NEURAL ACTIVITY SENSING

(71) Applicant: Oceanit Laboratories, Inc., Honolulu, HI (US)

(72) Inventors: Christopher J. Sullivan, Honolulu, HI (US); Ryan Y. Miyamoto, Honolulu, HI (US); Michael R. Hadmack, Honolulu, HI (US); Jeffrey Watamull, Honolulu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 1388 days.

(21) Appl. No.: 15/979,425

(22) Filed: May 14, 2018

Related U.S. Application Data

(60) Provisional application No. 62/505,251, filed on May 12, 2017.

(51) Int. Cl.
*A61B 5/00* (2006.01)
*A61B 5/05* (2021.01)
*A61B 5/24* (2021.01)

(52) U.S. Cl.
CPC .............. *A61B 5/4064* (2013.01); *A61B 5/05* (2013.01); *A61B 5/24* (2021.01)

(58) Field of Classification Search
CPC ........... A61B 5/388; A61B 5/24; A61B 5/361; A61B 5/4064; A61B 5/2415; A61B 5/05; A61B 5/031; A61B 5/369; A61B 5/14553; A61B 5/0295; A61B 5/245; A61B 5/291; A61B 5/31; A61B 5/0006
See application file for complete search history.

(56) References Cited

U.S. PATENT DOCUMENTS

| | | | | |
|---|---|---|---|---|
| 5,672,967 | A * | 9/1997 | Jensen | G01R 33/0206 324/253 |
| 7,672,707 | B2 * | 3/2010 | Takeda | A61B 5/245 600/409 |
| 8,934,965 | B2 * | 1/2015 | Rogers | A61B 5/0036 600/545 |
| 9,037,224 | B1 * | 5/2015 | Fu | A61N 2/02 600/544 |
| 9,383,208 | B2 * | 7/2016 | Mohanty | H03B 5/30 |
| 9,716,322 | B2 * | 7/2017 | Holzheimer | H01Q 21/205 |

(Continued)

FOREIGN PATENT DOCUMENTS

| | | | | |
|---|---|---|---|---|
| EP | 2180828 A1 * | 5/2010 | | A61B 5/04004 |
| WO | WO-2007101343 A1 * | 9/2007 | | A61B 5/002 |

(Continued)

OTHER PUBLICATIONS

D. Aur, The Physical Mechanism in Epilepsy: Understanding the Transition to Seizure. Journal of Neuroscience Methods 200, 2011, pp. 80-85 (Year: 2011).*

*Primary Examiner* — Shahdeep Mohammed
*Assistant Examiner* — Marjan Saboktakin
(74) *Attorney, Agent, or Firm* — Fresh IP PLC; Clifford D. Hyra; Aubrey Y. Chen

(57) ABSTRACT

An unshielded, non-invasive, ambulatory neural activity sensing device includes an array of alternating H-field and E-field sensors and a processor configured to localize an electromagnetic signal using a combination of H-field and E-field sensor outputs from the H-field and E-field sensors.

23 Claims, 7 Drawing Sheets

(56) References Cited

U.S. PATENT DOCUMENTS

| | | | |
|---|---|---|---|
| 2007/0085534 A1* | 4/2007 | Seki | G01R 33/02 |
| | | | 324/248 |
| 2015/0022372 A1* | 1/2015 | Vosch | A61B 5/0002 |
| | | | 340/870.07 |
| 2016/0143541 A1* | 5/2016 | He | A61B 5/374 |
| | | | 600/407 |
| 2017/0100051 A1* | 4/2017 | Honkura | A61B 5/242 |
| 2017/0176547 A1* | 6/2017 | Honkura | G01R 33/0023 |
| 2017/0281086 A1* | 10/2017 | Donaldson | A61B 5/14542 |
| 2018/0199841 A1* | 7/2018 | Yang | A61B 5/24 |

FOREIGN PATENT DOCUMENTS

| | | | | |
|---|---|---|---|---|
| WO | WO-2013026749 A1 * | 2/2013 | | A61B 5/04008 |
| WO | WO-2016073985 A1 * | 5/2016 | | A61B 5/0436 |

\* cited by examiner

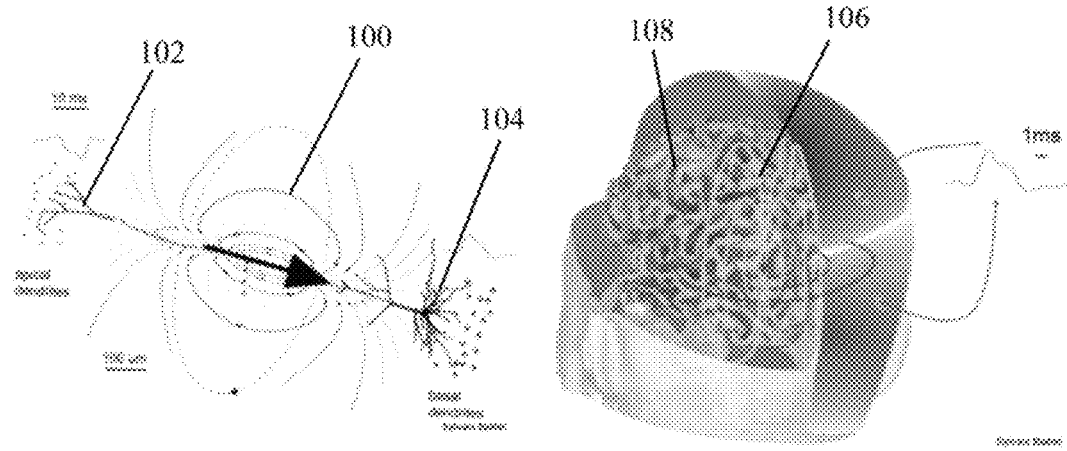
FIG. 1A PRIOR ART　　FIG. 1B PRIOR ART
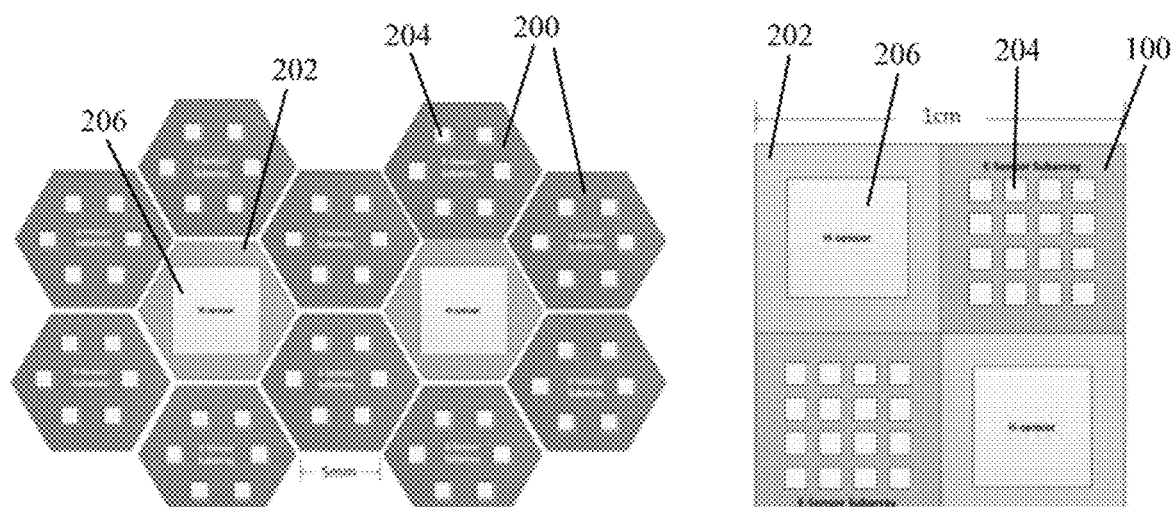
FIG. 2A　　FIG. 2B

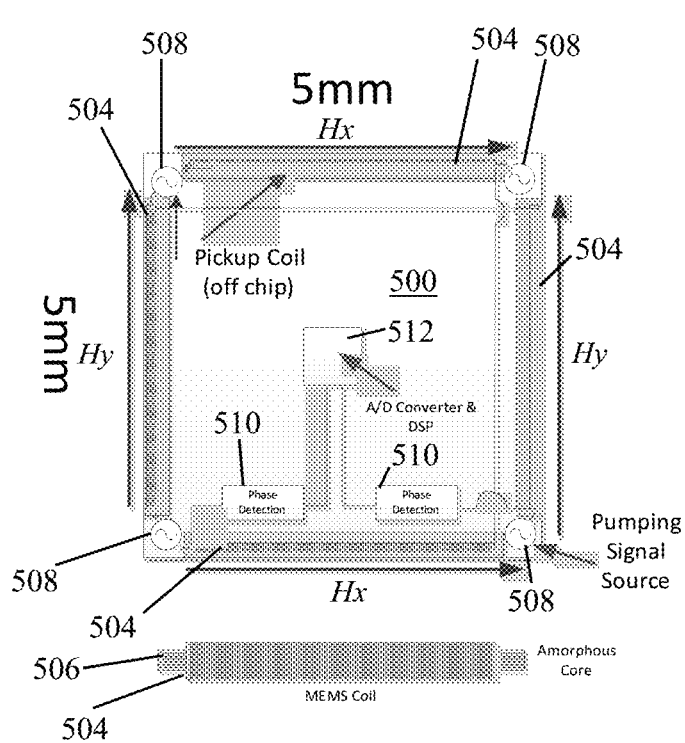
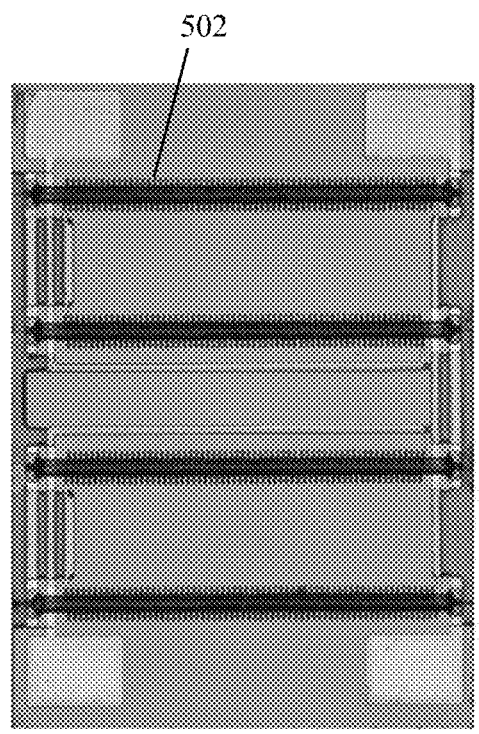
FIG. 5A
PRIOR ART
FIG. 5B
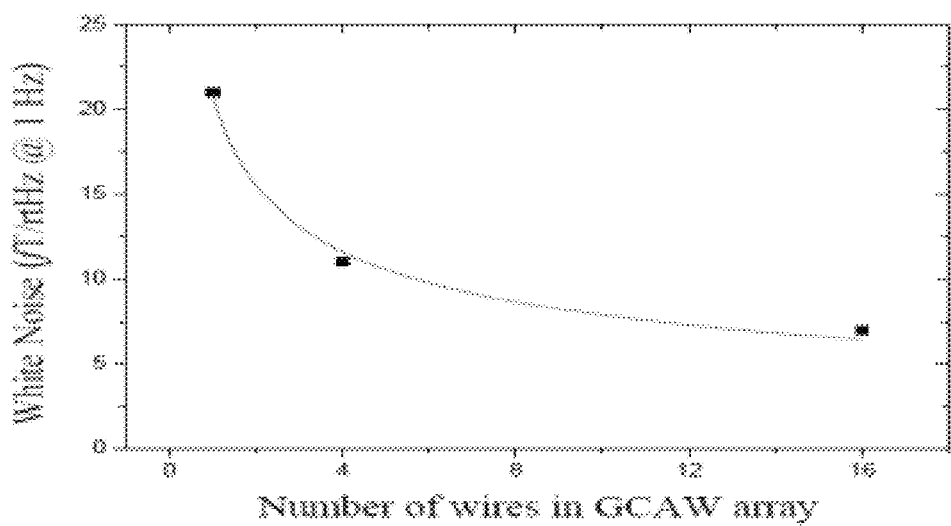
FIG. 6 (PRIOR ART)

METHODS AND APPARATUS FOR NON-INVASIVE NEURAL ACTIVITY SENSING

This application claims the benefit of U.S. Provisional Patent Application Ser. No. 62/505,251, filed May 12, 2017, which is hereby incorporated by reference herein in its entirety.

FIELD OF THE DISCLOSURE

This application relates generally to non-invasive neuronal sensing, brain-computer interfaces, and magnetic field sensing.

BACKGROUND

Neural Sensing

Past research and technologies have provided multiple methods for measurement of correlates of neural activity, some specifically for brain-computer interfaces (BCIs) and others for research or medical diagnoses. These technologies rely on measuring either the electro-magnetic properties of synaptic activity or the hemodynamic response to neuronal activity. These include electroencephalogram (EEG), magnetoencephalogram (MEG), electrocorticography (ECoG), positron emission tomography (PET), functional magnetic resonance imaging (fMRI) and functional near-infrared (fNIR).

Hemodynamic measurement techniques, namely fMRI, PET, and fNIR, analyze the content or flow of oxy- and deoxy-hemoglobin in cerebral tissue. Neuronal activity raises the metabolic demand in the active area which results in increased cerebral blood flow. While fMRI technology can produce relatively high spatial resolution images of these hemodynamic techniques, with sub-(2 mm)$^3$ voxels widely achievable, the spatial and temporal resolution are ultimately limited by the physiology rather than the technique. Studies have shown that tissue oxygenation increases are distributed over a few millimeters in diameter around the exact site of the neuronal activity and the hemodynamic response lags 2-3 seconds following stimulation.

Conversely, electromagnetic emissions of synaptic activity occur instantaneously and the existing electrical and magnetic measurement technologies have high temporal resolution (less than 1 ms) to capture these responses (FIGS. 1A-B). FIG. 1A illustrates the generation of electromagnetic fields 100 at the neuronal level by chemical transmission from apical 102 to basal 104 dendrites, with 10 ms response times at the dendrites 102, 104 and 100 µm in between, while FIG. 1B shows electromagnetic field 106 generation in the brain 108 at a macro level by combined neuronal activity, exhibiting a 1 ms response time. In general, MEG provides better sensitivity than EEG, with EEG typically requiring simultaneous activation of an approx. 6 cm$^2$ area in cerebral cortex while MEG only requires 3 cm$^2$. While there are neuron sensor technologies with higher resolution and sensitivity such as intracranial electroencephalography (iEEG) also known as electrocorticography (ECoG), they are invasive, thus with a limited sensing area.

The spatial resolution for EEG is on first-order limited by electrode size, with high density arrays general limited to 256 channels. While MEG systems achieve higher resolution (<10 mm), relatively expensive equipment is required for the widely-used superconducting quantum interference devices (SQUIDs) technique and shielding is necessary, eliminating the potential for deployment in an ambulatory scenario.

Patch clamp recordings allow for the study of the electrical response of a single neuronal cell or even specific cell features such as the basal dendrite. Various methods of applying the patch are used but all require the application of an electrode directly on the cell and another reference ground electrode in the area surrounding the cell to directly measure the electric potential elicited from cell excitation. While providing precise individual neuron activity measurements, patch clamp recordings are strictly a laboratory technique. Implementation in a human brain would require highly invasive and precise surgical techniques, leading to major obstacles in its experimental use in the human brain.

Finally, optogenetic approaches are limited to laboratory studies employing genetically altered transparent subjects.

Electric Field Encephalography

Electromagnetic field encephalography (EMFEG) deviates from the currently used non-invasive neural activity sensing technologies. This technique combines measurement of electric and magnetic fields at the scalp surface to provide signals that result from cognitive function. The approach assumed by this technique can detect low latency, highly sensitive and high resolution signals generated by neuronal activity.

While EEG systems have been developed and in use for many years, electric field encephalography (EFEG) has only recently received more attention. Electric field measurements are vector measurements, and by their nature they are more resolved (in direction) than potential measurements. Petrov and Sridhar investigated expected EFEG signal strength from the human brain and showed that the electric fields generated by cortical sources are more focused than the associated potentials, making EFEG a more localized measurement than EEG. The spatial resolution achieved is essentially limited by the sensor footprint. While Petrov and Sridhar identified fiber optic sensors with 1 mV/m sensitivity as a potential sensor, they estimate that electric field sensors with sensitivity on the order of 100 µV/m to 10 µV/m would be required to provide sufficient sensitivity for brain signal measurement. In addition to this sensitivity requirement, the sensor must be able to measure different components of the field, i.e., elevation and azimuth components.

Currently, a sensor with this level of sensitivity is not available to allow for the implementation of such a measurement system. However, such a measurement system would not be affected by skin impedances, therefore eliminating the need for skin preparation as required for EEG. Additionally, these electric field measurements could provide signal dimensions and components beyond just amplitude, including depth measurements, potentially offering additional components with which to distinguish and characterize neural activity and enabling the possible isolation and identification of activity in different cortical layers.

Magnetic Field Encephalography

In uncovering the cognitive information encoded in non-invasive, scalp surface measurements, the greater the number of signals and patterns, the greater the accuracy that can be achieved in characterizing the underlying neural activity. Electric field measurements can provide valuable information for this decoding but coupling with magnetic field measurements can provide useful features for neural activity characterization that are lacking in electric field data.

Aside from the higher sensitivity and spatial resolution achieved with MEG, magnetic field measurements can provide better correlates to sulcus activity than electric field measurements. However, the size and cost of the hardware traditionally used for SQUID techniques limit the use of MEG as the control input for brain-computer interfaces. In addition to the hardware expense, SQUID techniques also require extensive cooling and magnetic shielding of the MEG device that have rendered the fielding of magnetic field sensors impractical as a wearable, portable device.

Recent research has shown that alternate techniques can produce higher sensitivity magnetic field measurements while eliminating the need for cooling and shielding. For example, the scalar atomic magnetometer using two multipass optical cells developed by Sheng et al has shown a magnetic field sensitivity of 0.54 fT/Hz$^{1/2}$ and does not require cooling. The sensor measures an optical frequency shift caused by magnetic fields, called the Zeeman transition. The related Spin Exchange Relaxation Free (SERF) magnetometer is believed to be capable of sensitivities on the order of $10^{-18}$ Tesla. A chip-scale atomic magnetometer, based on optical spectroscopy of alkali atoms, is similarly uncooled and unshielded, and has a sensitive volume of 0.77 mm$^3$ able to detect somatosensory-evoked fields over C3. While these sensors provide sufficient magnetic field sensitivity, they lack the capability of sensing the direction of the field. In order to characterize neural activity, both amplitude and polarization measurements are required.

Needs exist for improved systems and methods of measuring neuronal activity.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In certain embodiments, the disclosed embodiments may include one or more of the features described herein.

A new unshielded, non-invasive, ambulatory neural activity sensing device includes an array of alternating H-field and E-field sensors and a processor configured to localize an electromagnetic signal using a combination of H-field and E-field sensor outputs from the H-field and E-field sensors. In some embodiments, the E-field sensors are EEG sensors and the H-field sensors are magnetic MEG sensors. In some embodiments, each of the H-field and E-field sensors has an area less than 1 cm$^2$. In some embodiments, each of the H-field and E-field sensors has an area less than 0.25 cm$^2$. In some embodiments, each E-field sensor has an area of 1 mm$^2$ or less.

In some embodiments, the processor is further configured to combine powers of signals from multiple of the E-field and/or H-field sensors to improve signal-to-noise ratio.

In some embodiments, the array of sensors is secured to a housing configured to be worn on a head of a human patient. In some such embodiments, the H-field sensors include pairs of coils in a gradiometer configuration spanning the head of the human patient when the housing is worn, and the processor is configured to use the pairs of coils to retrieve position information of a brain signal of the human patient using known positions of the coils relative to a center or other fixed reference position in the human patient's brain and brain signal amplitude measured at each coil to interpolate a location of a source of the brain signal.

In some embodiments, at least one of the H-field sensors is a fluxgate magnetometer-based gradiometer, having orthogonal fluxgate magnetometers utilizing a transformer constructed with two coils that share one magnetic core and are suitable for direct current H-field measurements.

In some embodiments, the E-field sensors are arranged in sub-arrays of six to sixteen individual sensors and one or more H-field sensors alternates with one of the sub-arrays of E-field sensors. In some such embodiments, the E-field sensors and the H-field sensors are situated on substrates, wherein each of the E-field sub-arrays is situated on its own substrate, the substrates are polygonal and are arranged such that each H-field sensor substrate is bordered on all sides by substrates bearing E-field sensor sub-arrays.

In some embodiments, at least one of the H-field sensors is an integrated circuit (IC) having four pumping signal sources connected to two pairs of off-chip MEMS pickup coils with amorphous wire cores forming two orthogonally polarized gradiometers. In some such embodiments, each pair of pickup coils is connected in series and located on opposite sides of the IC. In some such embodiments, the IC further includes phase detection circuits, and each pair of pickup coils is connected to a phase detection circuit. In some such embodiments, the IC further includes an analog-to-digital (A/D) converter and digital signal processor (DSP) and the A/D converter is configured to sample outputs of the phase detection circuits for orthogonal polarizations.

In some embodiments, at least one of the E-field sensors is an integrated circuit (IC) having four sets of orthogonal dipole antennas, two x-polarized and two y-polarized. In some such embodiments, the IC also includes four op-amps, each set of dipole antennas being connected to one of the op-amps, where each op-amp is configured to provide voltage gain to amplify a detected signal to a level suitable for an A/D converter to digitize the signal. In some such embodiments, the IC further includes an analog-to-digital (A/D) converter and digital signal processor (DSP), and the A/D converter is an eight-channel A/D converter configured to simultaneously sample four differential signals from the two x-polarized and two y-polarized dipole antennas and to aggregate the sampled signals and send them to the DSP for processing in the digital domain.

In some embodiments, the E-field sensor outputs comprise a plurality of n signals $s_0(k), s_1(k), \ldots s_n(k)$, where n is the number of E-field sensors, the processor is configured to represent these signals in a nonlinear system of equations:

$$\frac{s_0(k)}{s_1(k)} = \frac{(x(k)-x_1)^2 + (y(k)-y_1)^2 + (z(k)-z_1)^2}{x(k)^2 + y(k)^2 + z(k)^2}$$

$$\frac{s_0(k)}{s_2(k)} = \frac{(x(k)-x_2)^2 + (y(k)-y_2)^2 + (z(k)-z_2)^2}{x(k)^2 + y(k)^2 + z(k)^2}$$

$$\ldots$$

$$\frac{s_0(k)}{s_n(k)} = \frac{(x(k)-x_n)^2 + (y(k)-y_n)^2 + (z(k)-z_n)^2}{x(k)^2 + y(k)^2 + z(k)^2}$$

where $x_i, y_i, z_i$ are the spatial positions of the channels and $x(k), y(k)$ and $z(k)$ are the trajectory coordinates of the detected electric field at a point in time k, the processor is further configured to compress the nonlinear system of equations into a nonlinear system $f_j(x, y, z)=0, j=1, \ldots, n$ with $F=(f_1, f_2, \ldots fn)$ and apply a Newton-Raphson scheme is to compute the solution;

$$d_{n+1} = d_n - J^{-1} F(d_n), n \in N$$

and use the computed solution to determine a spatial trajectory (x(k), y(k), z(k)) for the detected electric field at each point in time k, and compute directivity of the detected electric field with the special trajectories thus determined.

These and further and other objects and features of the invention are apparent in the disclosure, which includes the above and ongoing written specification, with the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art.

FIGS. 1A-B illustrate physiological sources of electromagnetic fields.

FIG. 2A illustrates a honeycomb sub-array configuration and FIG. 2B illustrates a checkerboard sub-array configuration, according to an embodiment of the present invention.

FIG. 5A illustrates a gradiometer IC chip using a MEMS coil and FIG. 5B shows a MEMS pickup coil with amorphous wires, according to an embodiment of the present invention.

FIG. 6 shows theoretical white noise level of a multi-core orthogonal fluxgate magnetometer with CoFeSiB wire core.

DETAILED DESCRIPTION

Figure 3:
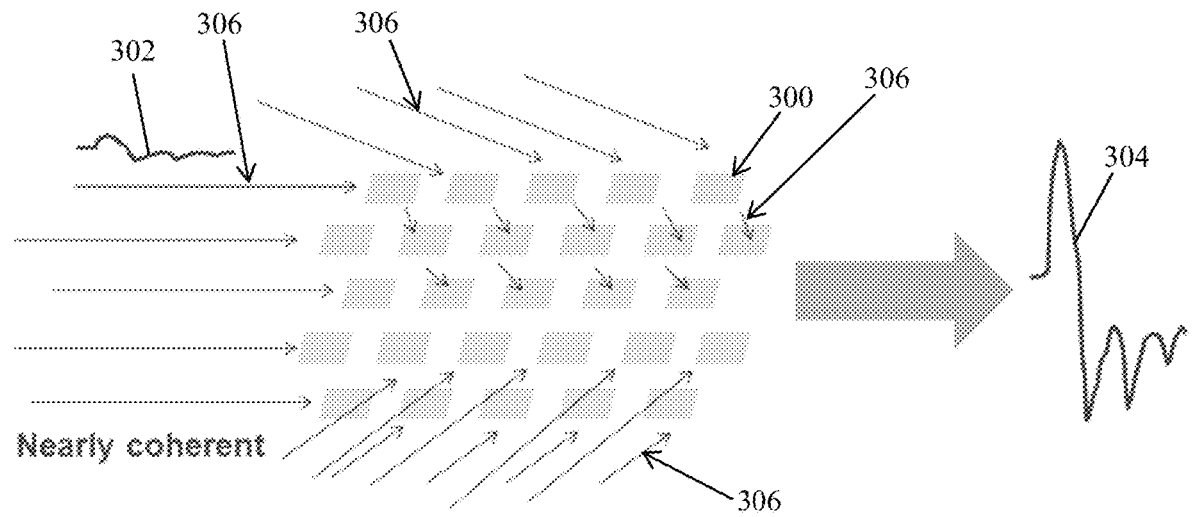
FIG. 3 illustrates power combining using a dense array of sensors, according to an embodiment of the present invention.

This disclosure details systems and methods for measuring neuronal activity. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted.

The description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an" and "the" are intended to include the plural forms as well, unless the context clearly indicates otherwise.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

A new method for ambulatory, wearable neuronal sensing and brain-computer interface combines high resolution electric and magnetic field measurements with inverse problem signal localization techniques. Low-noise, low-power, high-resolution EFEG sensing is achieved using chip-scale integrated sensors. Unshielded MFEG measurements are achieved using a novel sensor architecture that facilitates ambulatory measurements. The integrated sensors enable unprecedented spatial resolution and fieldability, further augmented by intelligent modeling to invert these data to the causal neuronal activity. The result is a system, termed a Mind Electromagnetic Localization Device (MELD), that is both non-invasive and fieldable in an ambulatory form factor that can produce mappings of single neuron activities at unconstrained cortical depths, previously only achieved through invasive microelectrode techniques.

Figure 4:
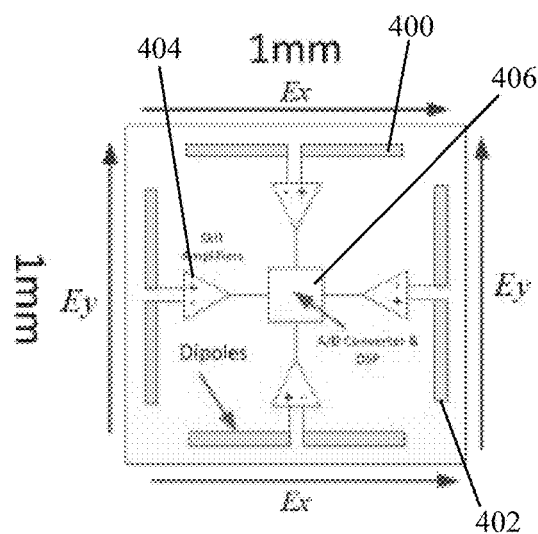
FIG. 4 illustrates an E-field sensor chip design, according to an embodiment of the present invention.

A high-performance probe enables electromagnetic field measurement with high sensitivity and high resolution without disturbing the field to be measured. A new E-field sensor chip (e.g. FIG. 4) accommodates four sets of orthogonal dipole antennas, two x-polarized and two y-polarized, frontend electronics and digital backend. FIG. 4 illustrates the E-field sensor chip design, in an embodiment of the present invention. The sensor chip serves as a single unit and a large number of them may be arranged in sub-arrays for system integration. Each chip accommodates two sets of orthogonal dipole antennas 400, 402, frontend electronics 404 and digital backend 406. The orthogonal antennas 400, 402 pick up both x- and y-polarizations of E fields. Each set of dipole antennas is connected to an op-amp 404, which provide very high voltage gain to amplify the detected signals to a level suitable for an A/D converter 406 to digitize the signal. An eight-channel A/D converter 406 simultaneously samples the four differential signals from the two x-polarized and two y-polarized antennas 400, 402 respectively, aggregates the sampled signals and sends them to the DSP to process in the digital domain.

For a target E-field of 10 uV/m, the 1-mm dipole generates a differential voltage output of 10 nV. This is sufficient signal amplitude for a modern low-noise Op-amp Integrated Circuit (IC), such as the Linear Technology LT1028 or LT1115 to capture electrical brain activity up to 50 Hz, particularly with implementation of a filter bank. The two antennas of the same polarization on the same chip enhance the signal-to-noise ratio (SNR) by 3 dB as the signal voltages from the two antennas separated by 1 mm are nearly identical but the noise from electronic circuits are uncorrelated.

For a resolution bandwidth to 10 Hz (up to alpha wave brain activity), the noise level of these Op-Amps is approximately 3 nV. In order to capture beta wave brain activity, it is necessary to cover frequencies up to 50 Hz. With the 50 Hz bandwidth, the noise level increases to approximately 7.1 nV, yet this is still lower than the target signal voltage. A filter bank can be implemented in the digital domain based on the sensor characterization to remove artifacts and acquire signals in different bands with reduced noise. If the E field does not have significant spatial variation within a sub-array, the detected signals from chips within a subarray can be combined to further increase the SNR.

Since the signal bandwidth of interest is very small, to avoid the high 1/f (pink) noise close to DC, Silicon-germanium (SiGe) BiCMOS technology may be used to design the circuit and SiGe transistors, which have much smaller 1/f noise compared to metal-oxide-semiconductor field-effect transistors (MOSFET), may be used for the frontend Op-Amp circuit 404. Because the antennas are integrated on chip, Silicon on insulator (SOI) process with low loss substrate may be used. Alternatively, Indium Phosphide (InP) heterojunction bipolar transistor (HBT) technology, which has very low 1/f noise and semi-insulating substrate, may be used.

For the H-field measurement, an inductive coil sensor is not suitable, as the sensitivity is proportional to the frequency being measured. A novel H-field sensor employs a fluxgate magnetometer-based gradiometer design. Fluxgate magnetometers utilize a transformer constructed with two coils that share one magnetic core and are suitable for even direct current (DC) H-field measurements. The nonlinear permeability of the magnetic core enables high-sensitivity measurement, as the core can be saturated and enter the nonlinear region even with a small magnetic field. The gradiometer design does not require magnetic shielding to detect weak magnetic fields. Amorphous wire-based fluxgate magnetometer gradiometers suppress uniform magnetic fields, allowing for unshielded measurement of relatively weak near-field H-fields. Further discrimination of H-fields can then be performed as part of source localization. The sensitivity of the novel H-field sensor is as low as 10 fT/$\sqrt{Hz}$.

In embodiments, the invention integrates electric field and magnetic field sensors into a module which serves as a sub-array (FIGS. 2A-2B). FIG. 2A illustrates a honeycomb sub-array configuration and FIG. 2B illustrates a checkerboard sub-array configuration. The smaller yellow boxes 204 represent E-sensors, while the larger tan boxes 206 represent H-sensors. The surrounding, blue/green material 200, 202 represents substrate material. Power combining of signals from multiple sensor elements improves signal-to-noise ratio. Moreover, the use of an array allows for spatiotemporal measurement of the electromagnetic field distribution generated by neuron firings. A dense array of sensors maximizes the number of sensors that can capture the field caused by a neuron or a group of neurons (FIG. 3); however, coupling between sensors becomes not negligible. Thus, it is necessary to reduce the coupling or/and take the coupling effect into account when the source locations are determined. FIG. 3 illustrates power combining using a dense array of sensors 300, and the resulting improvement in signal-to-noise ration from input 302 on the left to output 304 on the right. The light blue parallelograms 300 represent sensors, while the thin blue arrows 306 represent an incoming signal.

Pairs of coils in a gradiometer configuration spanning the head may be used to retrieve position information of brain signals. If signal amplitude, V, is measured at two locations: V1 410 at position x=+L and V2 412 at position x=−L along the x-axis, with the brain center at position x=0, then the position where the signal originated is given by x=(V1−V2)/V2, and similarly for the y-axis with two more sensors. A precision measurement of V1 and V2 is challenging, so instead the coils may be connected in anti-series, to null out the common mode and make a differential measurement Vx−=V1−V2.

To compute the absolute position either V1 or V2 is needed for normalization, which may be obtained by switching one of the gradiometer coils out of the circuit so that just V2 is measured or reversing the polarity of the second coil so that the gradiometer signal becomes Vx+=V1+V2. In either of these two scenarios, a circuit may be toggled back and forth between the sum and difference state at ¹⁄₁₀ of the excitation frequency and still maintain 1 kHz BW for sensing, but measure both sum and difference for the gradiometer, yielding absolute position between the sensor heads. With 4 sensors 90° apart this system can localize within the x-y plane. Extending this concept to a larger number of sensors in various complex wiring configurations yields higher spatial resolution and three-dimensional positioning information. A neural net may be used to obtain a large amount of information from this data for N gradiometers radially around the head.

The invention's electric field sensor chip is much smaller than its magnetic counterpart; therefore, the sub-array of electric field sensors can be extremely dense. One approach to remedy the coupling issue is to design the array as a whole, instead of designing an element neglecting the coupling effect. This is a common approach adopted in phased array design. For magnetic sensing, a 2D 32-element array with large spacing (4 cm) has been successfully demonstrated for magnetocardiogram applications. In order to further reduce the spacing, packaging must be improved.

FIGS. 5A-5B show a drawing of the gradiometer IC design 500 along with a photo of a prior-art microelectromechanical system (MEMS) coil 502, respectively. The chip is connected to two pairs of off-chip MEMS pickup coils 504 with amorphous wire cores 506, thus making two orthogonally polarized gradiometers. Amorphous wires with a diameter of 30 m were used. Thicker amorphous wires may provide higher sensitivity as the flux change volume in the magnetic core is proportional to the cross-sectional area of the core. Coil fabrication becomes difficult with thick amorphous wires, limiting commercial availability of such wires above 30 μm diameter.

Four pumping signal sources 508 connected to the amorphous wires are integrated on-chip. Two pickup coils 504 on opposite sides of the chip are connected in series and then connected to a phase detection circuit 510. The outputs of the phase detection circuits for orthogonal polarizations are sampled by the A/D converter 512. Similar to the E-field sensor chip, SiGe BiCMOS SOI process may be used to reduce the phase noise and substrate noise.

The mathematical innovation—applied effectively in quantum theory but never yet in neuroscience—that enables the information represented by the gradients independent vector fields (E-field and H field) is the "Schur product" of the matrices; this operation effectively maps corresponding entries of the two gradient fields multiplicatively and component-wise, representing the fact, informally stated, that the MELD measurements of the electric and magnetic fields contribute jointly to increased resolution of source localization. Let J be the Jacobian for the magnetic field B measured by MELD.

$$J = \begin{bmatrix} \frac{\partial B_x}{\partial x} & \frac{\partial B_y}{\partial x} & \frac{\partial B_z}{\partial x} \\ \frac{\partial B_x}{\partial y} & \frac{\partial B_y}{\partial y} & \frac{\partial B_z}{\partial y} \\ \frac{\partial B_x}{\partial z} & \frac{\partial B_y}{\partial z} & \frac{\partial B_z}{\partial z} \end{bmatrix}$$

B is a vector field with magnitude and direction defined for all points in space. With unit vectors, i, j, k on the x-, y-, z-axes, B can be expressed as $B=B_x i+B_y j+B_z k$. The gradient of B is denoted $\nabla B$; $\nabla B$ is the Jacobian (here a matrix of partial derivatives of the three principal components of B (Bx, By, Bz) with respect to the three cardinal directions (x, y, z)).

Let $\nabla D$ be the matrix for the E-field (measured by MELD or some other sensor (e.g., EEG)) or a vector for "spike directivity". Because MELD generates the Schur product of electric and magnetic Jacobians, the resolution is, at minimum, a multiplicative of the resolutions of EEG and MEG. Thus, if the resolution of EEG (with 70 channels) and MEG is on the order of centimeters, the resolution of MELD is on the order of microns (~100 given 2000 channels, but improvable to ~10). The Schur product represents the trapdoor information y that reduces the one-way (uninvertible) function $f(x)$ (i.e., the function from sources to signal(s)) measured by MELD to an invertible (intelligible) two-way function: each source (i.e., each neuron or cluster of neurons) is uniquely defined in the Schur product, thus localizing the sources with maximum spatial resolution. To understand neural computation, it is necessary to zoom-in on intracellular structures and processes (DNA is proof that this level can implement a Turing machine architecture). In this Turing approach, discrete charges (e.g., NA+, K+, Cl−, Ca2+)—generative of electric and magnetic fields—interact to perform computations. Charges can read, write, and store information in their spatial distribution (and directivity) at the molecular level (e.g., information can be encoded in proteins). Importantly these computations (e.g., spike directivity, protein geometry, etc.) may be decoded from their electric and magnetic fields (i.e., the function from charges to fields is not uninvertible), but only by a sensor with sufficiently high sensitivity and resolution. Thus, a sensor providing these high-sensitivity, high-resolution electromagnetic field measurements enables the decryption of neural computation.

Spike directivity represents the movement of intraneuronal charges. Ions such as $K^+$, $NA^+$, $Cl^-$, $Ca^{2+}$ carry electric charges generative of electric fields. The ionic flux under the influence of electric field and concentration gradient is computed in the Nernst-Planck equation. The interactions of these fluxes (and fields)—and interactions with the fields generated by ((de)polarized) macromolecules are described by a standard Hamiltonian formalism:

$$\frac{dq}{dt} = \frac{\partial H}{\partial p} \text{ and } \frac{dp}{dt} = -\frac{\partial H}{\partial q}$$

Here p=q can be written in the form of an action angle variable:

$$H = \sum_{I=1,N} H_0(I_1) + \varepsilon V(I_1, I_2, \ldots I_N, \theta_1, \theta_2, \ldots \theta_N)$$

Here, N represents the degree of freedom and $H_0$ is the unperturbed dynamics (i.e., non-interacting charges). With perturbation, there exists a condition for internal nonlinear resonances:

$$n_1\omega_1(I_{IO})+ \ldots +n_N\omega_N(I_{NO})=0$$

Here $n \in N$. Chaotic dynamics emerge if perturbation energy is higher than the energy difference between the nearest neighboring unperturbed resonant orbits ($\Delta H_i > E_{i+1} - E_i$).

This Hamiltonian is the foundation for computing directivity. First it is necessary to compute the charge trajectories. Let $s_0(k)$, $s_1(k)$, $s_2(k)$, $s_3(k)$, $k \in N$, be the signals from four channels measuring the trajectories of charges. This toy model has four channels for expository convenience. MELD contains 2000 channels, increasing sensitivity, resolution, and explanatory power. These signals are then represented in a nonlinear system of equations:

$$\frac{s_0(k)}{s_1(k)} = \frac{(x(k)-x_1)^2 + (y(k)-y_1)^2 + (z(k)-z_1)^2}{x(k)^2 + y(k)^2 + z(k)^2},$$

$$\frac{s_0(k)}{s_2(k)} = \frac{(x(k)-x_2)^2 + (y(k)-y_2)^2 + (z(k)-z_2)^2}{x(k)^2 + y(k)^2 + z(k)^2},$$

$$\frac{s_0(k)}{s_3(k)} = \frac{(x(k)-x_3)^2 + (y(k)-y_3)^2 + (z(k)-z_3)^2}{x(k)^2 + y(k)^2 + z(k)^2}$$

Here $x_i$, $y_i$, $z_i$ are the spatial positions of the channels and x(k), y(k) and z(k) are the trajectory coordinates of the charge that need to be solved for. These equations can then be compressed into a nonlinear system $f_j(x, y, z)=0$, $j=1, \ldots, 3$ with $F=(f_1, f_2, f_3)$. A Newton-Raphson scheme is then applied to compute the solution:

$$d_{n+1}=d_n-J^{-1}F(d_n), n \in N$$

where d is the distance between the tips of tetrodes. The Jacobian J of function F is given:

$$J = \begin{pmatrix} \frac{\partial f_1}{\partial x} & \frac{\partial f_1}{\partial y} & \frac{\partial f_1}{\partial z} \\ \frac{\partial f_2}{\partial x} & \frac{\partial f_2}{\partial y} & \frac{\partial f_2}{\partial z} \\ \frac{\partial f_3}{\partial x} & \frac{\partial f_3}{\partial y} & \frac{\partial f_3}{\partial z} \end{pmatrix}$$

In short, at each discrete moment k, from the signals $s_1(k)$, $s_2(k)$, $s_3(k)$, $s_4(k)$, the spatial trajectory (x(k), y(k), z(k)) is determined given a solution $d_{n+1}$ for this nonlinear system. With the trajectories thus determined, directivity can be computed. Given the trajectory coordinates (x(k), y(k), z(k)), the matrix $P \in \mathfrak{R}^{n \times 3}$, is constructed:

$$P = \begin{pmatrix} x(1) & y(1) & z(1) \\ \cdots & \cdots & \cdots \\ x(n) & y(n) & z(n) \end{pmatrix}$$

For each signal the centroid of the data $\mu=E(P^T)$ is computed to form the matrix $P_{tr}$ of translated points $P_{tri}=p_i-\mu_i$, i=1, 2, . . . , n. From this can be formulated the all-important singular value decomposition:

$$P_{unx3} = U_{nxn}S_{nx3}V_{3x3}^T$$

$$S = \begin{pmatrix} s_1 & & & \\ & s_2 & & \\ & & s_3 & \\ \cdots & \cdots & \cdots & \cdots \end{pmatrix};$$

$$U = (u_1, u_2, \ldots, u_n);$$

$$V = (v_1, v_2, v_3);$$

From this we simply calculate the largest singular value S and deduce from V the corresponding right singular vector that represents direction cosines of the best linear approximation. This directivity vector (calculated from the electric field measured by MELD) is represented as a matrix ∇D so as to be concatenated with the Jacobian J for the magnetic field B measured by MELD to arrive at the concatenation of the E-field with the H-field.

An example of similar mathematical calculations can be found in Aur, D. 2011. *The Physical Mechanism in Epilepsy: Understanding the Transition to Seizure*. Journal of Neuroscience Methods 200: 80-85, which is hereby incorporated by reference herein in its entirety.

A high-performance probe enables electromagnetic field measurement with high sensitivity and high resolution without disturbing the field to be measured. Based on modeling results and MEG data, the minimum required sensitivities for electric and magnetic fields are 10 uV/m and 10 fT/√Hz respectively. The resolution of a near-field probe largely depends on its aperture dimension. Higher resolution however typically comes at the expense of sensitivity. Therefore, it is necessary to find an optimal point in terms of sensitivity and resolution. In addition, the capability to measure the direction of the field is necessary to accurately capture the trajectory of a neuron firing. Therefore, a highly polarized probe design is required. In order to meet these requirements, a state-of-the-art system on chip (SoC) design and process has been adopted, as well as advanced substrate materials and architecture such as SOI to eliminate stray current within the substrate. This is necessary to maximize signal to noise ratio with a limited sensor size. Furthermore, the use of tiny sensors enables power combining and focusing using a dense array of sensors. Both E-field and H-field measurements are used.

The sensitivity of an inductive coil sensor is proportional to the frequency that is being measured. Therefore, the inductive coil sensor is not suited for neuron activity sensor applications in which measurement of low frequency signals is required. By contrast, the fluxgate magnetometer allows for measurement of DC or low-frequency fields. The fluxgate magnetometer uses a transformer constructed with two coils sharing one magnetic core. Nonlinear permeability of the magnetic core enables high-sensitivity measurement, as the core can be saturated and enter the nonlinear region even with a small magnetic field. The core material must be highly permeable and very low noise in order to provide high sensitivity. Recent progress in material science and process enables extremely compact yet sensitive magnetic orthogonal fluxgate sensors using amorphous wires with a small diameter, achieving a noise level as low as 10 pT/√Hz at 2 Hz. Employing a 10-wire glass-coated amorphous wire (GCAW) core can reduce noise down to 6 pT/√Hz. An orthogonal fluxgate magnetometer with a GCAW core (FIG. 6) may achieve around 7.5 fT/√Hz at 1 Hz according to theory as the number of wires in the GCAW array increases to 16, an improvement of about three orders of magnitude.

TABLE 1

Performance comparison of orthogonal fluxgate sensors.

| | Resolution/ Sensitivity | Frequency (Hz) | Noise level | Size(mm) | Remarks |
|---|---|---|---|---|---|
| Candidi [36] | — | 0.02-5 | 0.26 nT | d0 = 4, d1 = 3.8 L = 144 | Tubular core |
| Gise [51] | —/50 mV/μT | DC | — | D = 6.35, L = 63.5 | Rod core |
| Sasada [57] | —/230 mV/μT | <51 | 0.1 nT/rtHz@10 Hz | Dw = 0.12, L = 20 | Wire core |
| Papersno [58] | 0.1 nT/1.1 mV/μT | <4.9 | 10 pT/rtHz@2 Hz | Dw = 0.12, L = 20 | Wire core |
| Goleman[55] | 121 mV/μT | <200 | 50 μT/rtHz@10 Hz | 1 × 0.013, L = 50 | Ribbon |
| Zorlu [56] | 510 μV/mT | 10 | 95 nT/rtHz@1 Hz | Dw = 0.016 × 0.01 L = 1 | Rod core |
| Aichi sensor [60] | 5 nT/1600 mV/μT | 0.3-5 | — | Dw = 0.02, L = 1 1 × 0.5 | Wire core Pickup coil |

While the fluxgate magnetometer provides sufficient sensitivity for neuron activity sensing, it generally requires magnetic shielding to isolate the Earth's magnetic field. A gradiometer using orthogonal fluxgate magnetometers may be employed to eliminate the need for magnetic shielding. The gradiometer is a device commonly used in geophysical surveys to measure the gradient of a magnetic field instead of the field itself. A gradiometer using amorphous-based fluxgate magnetometers suppresses a uniform magnetic field, thus eliminating the need for magnetic shielding to detect a weak magnetic field.

Figure 7A:
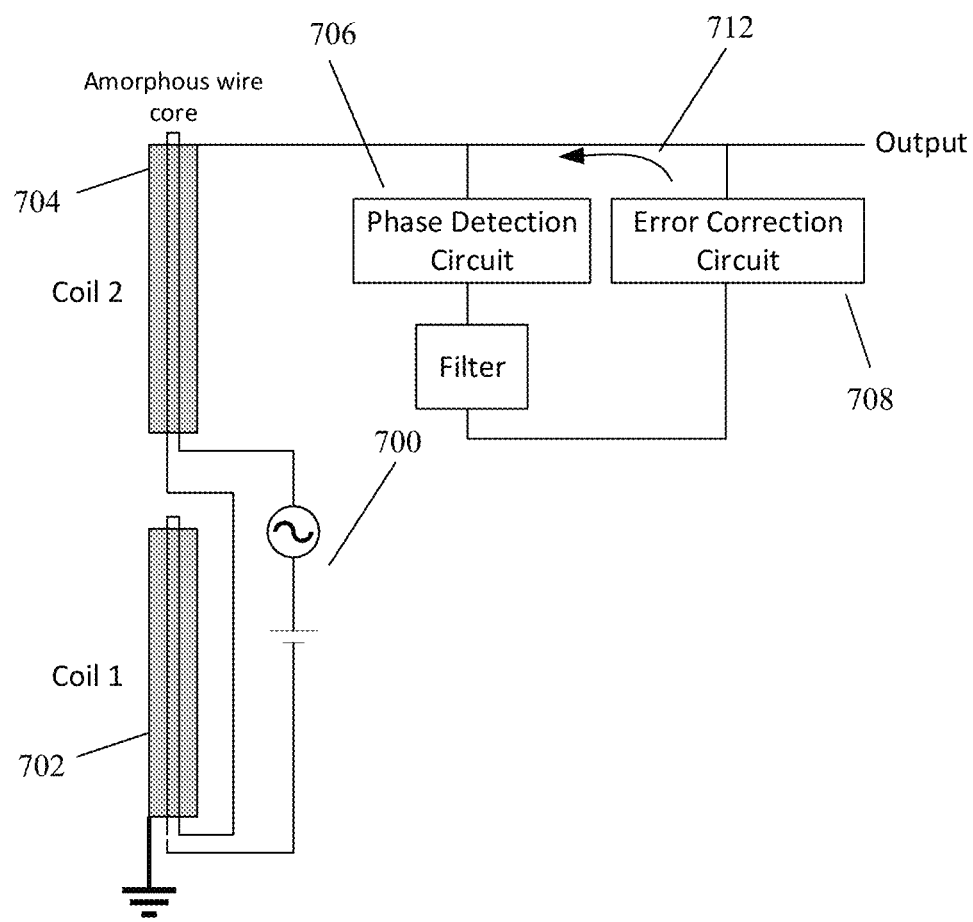
FIGS. 7A and 7B illustrate gradiometers using orthogonal fluxgate magnetometers with analog phase detection circuitry and digital signal processing, respectively, according to embodiments of the present invention.
Figure 7B:
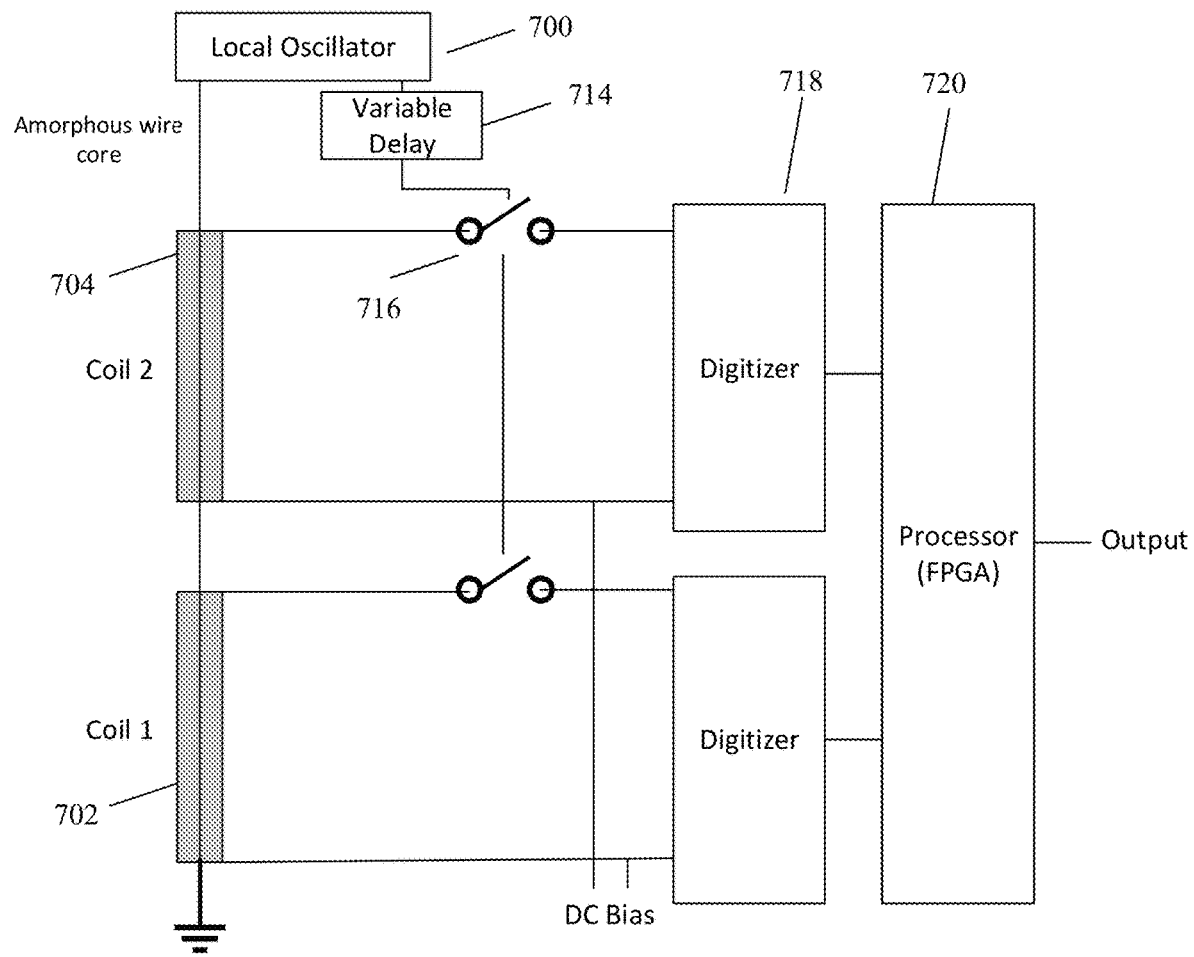

FIGS. 7A-7B show functional block diagrams of gradiometers. In the design in FIG. 7A, a 100-kHz pumping signal 700 is applied to the pick-up coils 702, 704 with amorphous wire cores. The output voltage of the secondary coil 704 is measured using a phase sensitive diode (PSD) 706. The diode response is then applied to a feedback resister 708 after suppressing high-frequency components caused by switching in the PSD with smoothing filter 710. As a result, a feedback current 712 flows back into the coil 704. Since the two coils 702, 704 'see' slightly different magnetic fields due to the spacing in between, the feedback current 712 causes a voltage difference between the coils.

The design in FIG. 7B takes advantage of digital signal processing. Pulse generator 700 supplies a signal to coils 702, 704 as in FIG. 7A. A variable delay is introduced by delay element 714 and the signals flow through analog switches to digitizers 718 and on to field programmable gate array (FPGA) 720.

Figure 8:
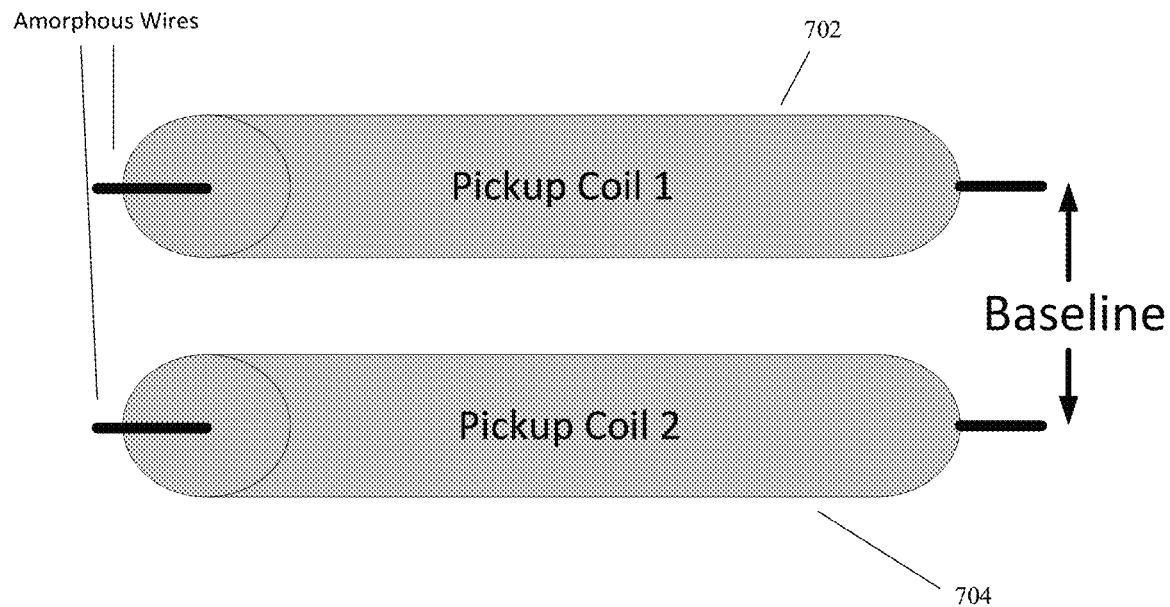
FIG. 8 illustrates a parallel configuration of the gradiometer using orthogonal fluxgate magnetometers, according to an embodiment of the present invention.
Figure 9:
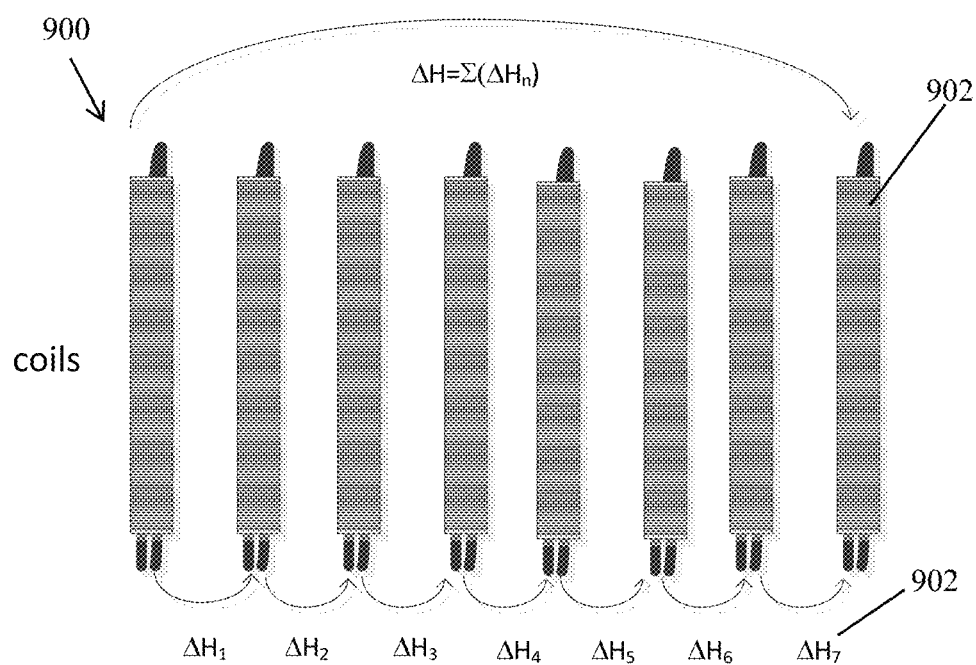
FIG. 9 illustrates variable spacing using a different pair of gradiometer coils in an array, according to an embodiment of the present invention.

The FIG. 7A design uses coils 702, 704 with a length of 30 mm and a spacing of 5 cm to achieve a noise level of 2 pT/√Hz, as illustrated in FIG. 8. The sensitivity and resolution can be further improved using smaller spacing between the coils, which however results in the inability to detect a signal source in a deeper area in the brain. This problem may be overcome by using an array of gradiometers 900 as shown in FIG. 9. Each pair of adjacent coils 902 functions as a separate gradiometer, measuring the magnetic field gradient 904 between those two coils. The array integrates the gradient of a magnetic field, thus enabling detection of a signal source in a deeper part of the brain.

Figure 10:
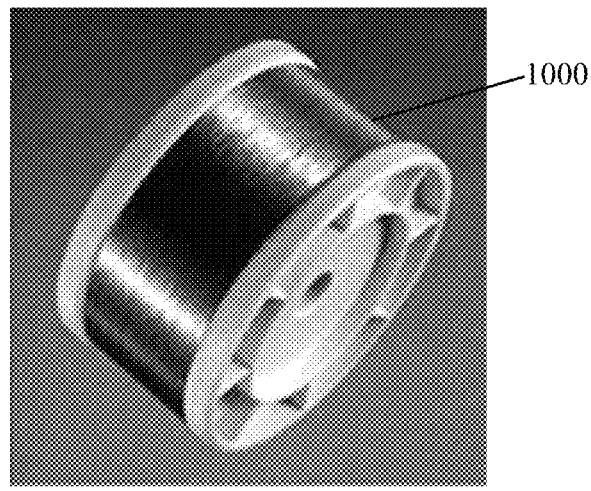
FIG. 10 illustrates a glass-coated amorphous micro-wire.

MELD may utilize amorphous micro-wire for sensor development. More specifically, amorphous alloy compositions e. g., $Co_{70.5}Fe_{4.5}Si_{15}B_{10}$; $Ni_{42}Fe_{28}Si_{10}B_{20}$, and borosilicate pyrex glass (Corning 7740) may be used. FIG. 10 shows a glass-coated amorphous micro-wire 1000. The magnetic alloy micro-wires are produced using a known specialized approach, commercially used for glass coated metal micro-wires for medical, electronics and aerospace industries, in which the morphology of the alloy is controlled to retain the amorphous state through rapid quenching of the alloy from a molten state. During the quenching process the alloy is in semi-equilibrium state, so an external field (magnetic or electric) can be applied to further modify the properties of the resulting alloys.

Generally, multi-wires are assembled manually under a microscope using ultra-precision tools, however, establishing a uniform and tight bonding between the wires is challenging. Hence, MELD may utilize a template-based approach for developing the multi-core micro-wires. The approach to fabricate the multi-core amorphous wires is a liquid metal infiltrating (LMI) process. Commercially available templates (alumina, zirconia, and cordierite honeycomb monolith), and metal/alloy powders may be used. As mentioned above, the multi-core alloy wires of compositions e.g., $Co_{70.5}Fe_{4.5}Si_{15}B_{10}$; $Ni_{42}Fe_{28}Si_{10}B_{20}$, may be fabricated.

Figure 11:
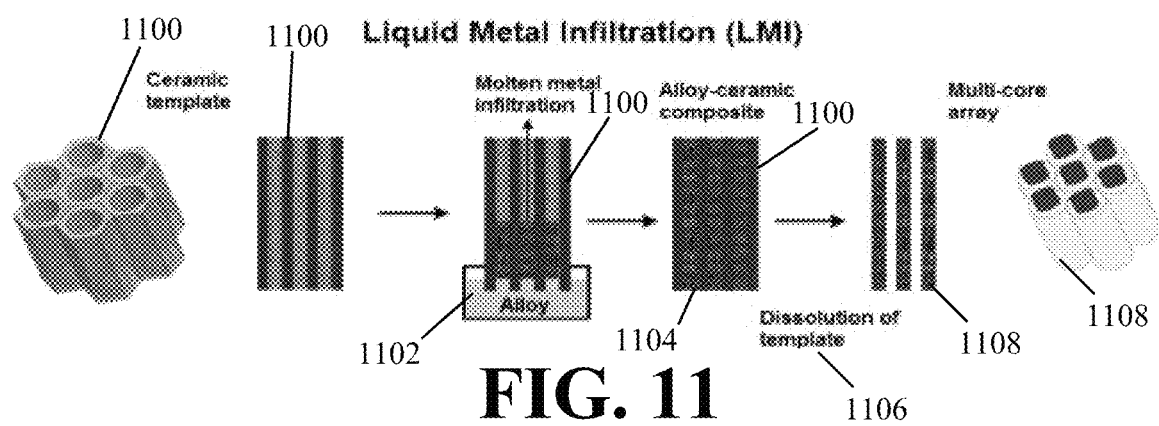
FIG. 11 illustrates the fabrication of multi-core wire using template-based liquid metal infiltration process, according to an embodiment of the present invention.

The ceramic template 1100 is filled by the liquid metal 1102 through capillary forces as shown in FIG. 11 after one end of the template 1100 is placed therein. The ceramic template sustains the high temperatures and liquid metal is non-reactive with the template material. Upon complete filling of the template the melt is allowed to cool to room temperature, leaving the template filled with solid metal 1004 prior to removing 1106 the template using an etching solution. The template is subsequently dissolved and multi-core wires 1108 are obtained after solvent evaporation. The multi-wires coalesce in the solution due to surface tension after the template is removed with etching solvent. The assembled wires are further treated with an acidic solution to improve the bonding and remove the contaminants from the etching process. The wires are characterized for morphology using a scanning electron microscope and for chemical structure using X-ray diffraction technique.

A digital backend comprising a multi-channel analog-to-digital converter (ADC) and a digital signal processor (DSP) and memory (see 512, FIG. 5A) is integrated on the same chip as the probe frontend electronics. The DSP is employed to conduct preliminary signal processing such as averaging and filtering in digital circuitry without affecting the analog part of the system.

Oversampling can be used to increase converter resolution, as the sampling speed required for neuron sensing is not high. On-chip sigma-delta ADCs with 24-bit resolution and a sampling speed of 10 kHz may be employed.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

What is claimed is:

1. An unshielded, non-invasive, ambulatory neural activity sensing device, comprising:
   an array of alternating magnetic field (H-field) and electric field (E-field) sensors; and
   a processor configured to localize an electromagnetic signal using a combination of H-field and E-field sensor outputs from the H-field and E-field sensors,
   wherein the H-field sensors are interspersed with the E-field sensors along a same surface,
   wherein the E-field sensors are arranged in sub-arrays of six to sixteen individual sensors and one or more H-field sensors alternates with one of the sub-arrays of E-field sensors,
   wherein the E-field sensors and the H-field sensors are situated on substrates, wherein each of the E-field sub-arrays is situated on its own substrate, wherein the substrates are polygonal and are arranged such that each H-field sensor substrate is bordered on all sides in a two-dimensional plane by substrates bearing E-field sensor sub-arrays, and
   wherein the device is unshielded.

2. The device of claim 1, wherein the E-field sensors are electroencephalogram (EEG) sensors and the H-field sensors are magnetoencephalogram (MEG) sensors.

3. The device of claim 1, wherein each of the H-field and E-field sensors has an area less than 1 $cm^2$.

4. The device of claim 1, wherein each of the H-field and E-field sensors has an area less than 0.25 $cm^2$.

5. The device of claim 1, wherein each E-field sensor has an area of 1 $mm^2$ or less.

6. The device of claim 1, wherein the processor is further configured to combine powers of signals from multiple of the E-field and/or H-field sensors to improve signal-to-noise ratio.

7. The device of claim 1, wherein the array of sensors is secured to a housing configured to be worn on a head of a human patient.

8. The device of claim 7, wherein the H-field sensors comprise pairs of coils in a gradiometer configuration spanning the head of the human patient when the housing is worn, wherein the gradiometer configuration is at least one of an parallel arrangement and an arrangement in series, wherein the processor is configured to use the pairs of coils to retrieve position information of a brain signal of the human patient using known positions of the coils relative to a center or other fixed reference position in the human patient's brain and brain signal amplitude measured at each coil to interpolate a location of a source of the brain signal.

9. The device of claim 1, wherein at least one of the H-field sensors is a fluxgate magnetometer-based gradiometer, comprising orthogonal fluxgate magnetometers utilizing a transformer constructed with two coils that are suitable for direct current H-field measurements, wherein the two coils share a same magnetic core.

10. The device of claim 1, wherein at least one of the E-field sensors is an integrated circuit (IC) with four sets of dipole antennas, wherein a first set in the four sets is orthogonally disposed with respect to a second set in the four sets such that the first set is arranged with its antennas disposed along a horizontal direction on the IC and the second set is arranged with its antennas disposed along a vertical direction on the IC, wherein a third set in the four sets is orthogonally disposed with respect to a fourth set in the four sets such that the third set is arranged with its antennas disposed along a horizontal direction on the IC and the fourth set is arranged with its antennas disposed along a vertical direction on the IC, wherein the first set is disposed parallel to the third set, wherein the second set is disposed parallel to the fourth set, and wherein two of the four sets are x-polarized and two of the four sets are y-polarized.

11. The device of claim 1, wherein measurements are obtained from the H-field sensors and the E-field sensors during unshielded operation of the device.

12. An unshielded, non-invasive, ambulatory neural activity sensing device, comprising:
an array of alternating magnetic field (H-field) and electric field (E-field) sensors; and
a processor configured to localize an electromagnetic signal using a combination of H-field and E-field sensor outputs from the H-field and E-field sensors,
wherein the H-field sensors are interspersed with the E-field sensors along a same surface,
wherein at least one of the H-field sensors is an integrated circuit (IC) comprising four pumping signal sources connected to two pairs of pickup coils, wherein the pickup coils are off of the IC and are micro-electromechanical system (MEMS) coils, and wherein the pickup coils comprise amorphous wire cores to form two orthogonally polarized gradiometers, and
wherein the device is unshielded.

13. The device of claim 12, wherein the two pairs of pickup coils comprises a first pair and a second pair,
wherein the first pair comprises a first coil and a second coil, wherein the second pair comprises a third coil and a fourth coil,
wherein the first coil is disposed on a first side of the IC, the second coil is disposed on a second side of the IC, the third coil is disposed on a third side of the IC, and the fourth coil is disposed on a fourth side of the IC,
wherein the first side is parallel to, and opposite, the second side, and wherein the third side is parallel to, and opposite, the fourth side,
wherein the first coil is connected in series to the second coil, and wherein the third coil is connected in series to the fourth coil.

14. The device of claim 13, wherein the IC further comprises phase detection circuits, wherein the first pair is connected to a first phase detection circuit of the phase detection circuits, and wherein the second pair is connected to a second phase detection circuit of the phase detection circuits.

15. The device of claim 14, wherein the IC further comprises an analog-to-digital (A/D) converter and digital signal processor (DSP) and the A/D converter is configured to sample outputs of the phase detection circuits for orthogonal polarizations.

16. An unshielded, non-invasive, ambulatory neural activity sensing device, comprising:
an array of alternating magnetic field (H-field) and electric field (E-field) sensors; and a processor configured to localize an electromagnetic signal using a combination of H-field and E-field sensor outputs from the H-field and E-field sensors,
wherein the H-field sensors are interspersed with the E-field sensors along a same surface,
wherein at least one of the E-field sensors is an integrated circuit (IC) with four sets of dipole antennas, wherein a first set in the four sets is orthogonally disposed with respect to a second set in the four sets such that the first set is arranged with its antennas disposed along a horizontal direction on the IC and the second set is arranged with its antennas disposed along a vertical direction on the IC, wherein a third set in the four sets is orthogonally disposed with respect to a fourth set in the four sets such that the third set is arranged with its antennas disposed along a horizontal direction on the IC and the fourth set is arranged with its antennas disposed along a vertical direction on the IC, wherein the first set is disposed parallel to the third set, wherein the second set is disposed parallel to the fourth set, and wherein two of the four sets are x-polarized and two of the four sets are y-polarized,
wherein the IC further comprises four op-amps, each set of dipole antennas being connected to one of the op-amps, wherein each op-amp is configured to provide voltage gain to amplify a detected signal to a level suitable for an A/D converter to digitize the signal, and
wherein the device is unshielded.

17. The device of claim 16, wherein the IC further comprises an analog-to-digital (A/D) converter and digital signal processor (DSP), wherein the A/D converter is an eight-channel A/D converter configured to simultaneously sample four differential signals from the two x-polarized and two y-polarized dipole antennas and to aggregate the sampled signals and send them to the DSP for processing in a digital domain.

18. An unshielded, non-invasive, ambulatory neural activity sensing device, comprising:
an array of alternating magnetic field (H-field) and electric field (E-field) sensors; and
a processor configured to localize an electromagnetic signal using a combination of H-field and E-field sensor outputs from the H-field and E-field sensors,
wherein the H-field sensors are interspersed with the E-field sensors along a same surface,
wherein the E-field sensor outputs comprise a plurality of n signals $s_0(k), s_1(k), \ldots s_n(k)$, where n is the number of E-field sensors, wherein the processor is configured to represent these signals in a nonlinear system of equations:

$$\frac{s_0(k)}{s_1(k)} = \frac{(x(k)-x_1)^2 + (y(k)-y_1)^2 + (z(k)-z_1)^2}{x(k)^2 + y(k)^2 + z(k)^2}$$

-continued
$$\frac{s_0(k)}{s_2(k)} = \frac{(x(k)-x_2)^2 + (y(k)-y_2)^2 + (z(k)-z_2)^2}{x(k)^2 + y(k)^2 + z(k)^2}$$

$$\ldots$$

$$\frac{s_0(k)}{s_n(k)} = \frac{(x(k)-x_n)^2 + (y(k)-y_n)^2 + (z(k)-z_n)^2}{x(k)^2 + y(k)^2 + z(k)^2}$$

wherein $x_i$, $y_i$, $z_i$ are spatial positions of channels and x(k), y(k) and z(k) are trajectory coordinates of a detected electric field at a point in time k;

wherein the processor is further configured to compress the nonlinear system of equations into a nonlinear system $f_j(x, y, z)=0$, $j=1, \ldots, n$ with $F=(f_1, f_2, \ldots f_n)$ and apply a Newton-Raphson scheme is to compute the solution:

$$d_{n+1} = d_n - J^{-1}F(d_n), \; n \in N$$

and use the computed solution to determine a spatial trajectory (x(k), y(k), z(k)) for the detected electric field at each point in time k, and compute directivity of the detected electric field with the special trajectories thus determined, and wherein the device is unshielded.

19. A neural activity sensing device comprising:
a plurality of interconnected hexagonal substrates comprising a first set of substrates and a second set of substrates;
a plurality of magnetic field (H-field) sensors, wherein one H-field sensor in the plurality of H-field sensors is connected to each substrate in the first set of substrates; and
a plurality of electric field (E-field) sensors, wherein six to sixteen E-field sensors in the plurality of E-field sensors are connected to each substrate in the second set of substrates,
wherein each side of each substrate in the first set of substrates is connected to, and bordered in a two-dimensional plane by, a substrate in the second set of substrates,
wherein one or more substrates in the first set of substrates alternates with one substrate in the second set of substrates,
wherein at least one of the plurality of H-field sensors comprises a transformer constructed with two coils that share one magnetic core,
wherein at least one of the plurality of E-field sensors comprises four sets of orthogonal dipole antennas, a first two sets of the four sets being x-polarized and a second two sets of the four sets being y-polarized, and
wherein the device is unshielded.

20. A neural activity sensing device comprising:
a plurality of electric field (E-field) sensors, wherein one E-field sensor in the plurality of E-field sensors is connected to a first polygonal substrate, and
a plurality of magnetic field (H-field) sensors, wherein a subset of H-field sensors in the plurality of H-field sensors is connected to a second polygonal substrate,
wherein the first polygonal substrate is connected to the second polygonal substrate by at least one side of the first polygonal substrate, the first polygonal substrate and the second polygonal substrate forming a single layer,
wherein at least one of the plurality of H-field sensors is an integrated circuit (IC) comprising four pumping signal sources connected to two pairs of pickup coils, wherein the pickup coils are off of the IC and are micro-electromechanical system (MEMS) coils, and wherein the pickup coils comprise amorphous wire cores to form two orthogonally polarized gradiometers,
wherein the device is unshielded.

21. The device of claim 20, wherein, when the first and the second polygonal substrates are laid flat, the first polygonal substrate is connected in a same two-dimensional plane to the second polygonal substrate.

22. The device of claim 20, wherein the one E-field sensor that is connected to the first polygonal substrate is laterally adjacent to the subset of H-field sensors that is connected to the second polygonal substrate.

23. The device of claim 20, further comprising:
a processor configured to localize an electromagnetic signal using a combination of H-field and E-field sensor outputs from the plurality of H-field sensors and the plurality of E-field sensors,
wherein the plurality of H-field sensors are interspersed with the plurality of E-field sensors along a same surface.

* * * * *